United States Patent [19]
Lancaster

[11] Patent Number: 4,578,072
[45] Date of Patent: Mar. 25, 1986

[54] LEAK RESISTANT DIAPER OR INCONTINENT GARMENT

[75] Inventor: Eugene P. Lancaster, Gig Harbor, Wash.

[73] Assignee: Weyerhaeuser Company, Tacoma, Wash.

[21] Appl. No.: 559,597

[22] Filed: Dec. 8, 1983

[51] Int. Cl.$^4$ ............................................. A41B 13/02
[52] U.S. Cl. .............................. 604/385 A; 604/385 R; 604/389; 604/390
[58] Field of Search ......... 604/385, 389, 390, 392–394

[56] References Cited

U.S. PATENT DOCUMENTS

| | | |
|---|---|---|
| 2,273,542 | 2/1942 | Tasker . |
| 3,603,314 | 9/1971 | Aberg ................................. 604/381 |
| 3,794,033 | 2/1974 | Ryan . |
| 3,800,796 | 4/1974 | Jacob ................................. 604/390 |
| 3,860,003 | 1/1975 | Buell . |
| 4,041,949 | 8/1977 | Kozak ................................. 604/390 |
| 4,050,462 | 9/1977 | Woon et al. . |
| 4,063,559 | 12/1977 | Tritsch ............................... 604/390 |
| 4,182,334 | 1/1980 | Johnson .............................. 604/392 |
| 4,253,461 | 3/1981 | Strickland et al. . |
| 4,317,449 | 3/1982 | Nowakoski ......................... 604/390 |
| 4,336,803 | 6/1982 | Repke ............................. 604/385 A |
| 4,430,086 | 2/1984 | Repke ............................. 604/385 A |

Primary Examiner—C. Fred Rosenbaum
Assistant Examiner—Sherri E. Vinyard

[57] ABSTRACT

The invention relates to a leak resistant disposable diaper or incontinent brief particularly suitable for adult wear. The garment is from about two to three times as long as it is wide so that the sides of the wearer are not covered. Each end of the garment has a relatively long flap formed by extensions of the envelope retaining the pad of absorbent material. The absorbent pad itself is trimmed generally in the form of an hourglass. However, the cutout side portions are located forward of the transverse centerline of the pad. Also, the forward edge of the cutouts does not expand as rapidly to full width as does the back edge to allow a better fit in the groin area. Elastic strips are located adjacent to the edges of the pad and run the full length of the product. Relatively long attachment straps are anchored to the back flap and form the means of holding the garment on the wearer. The adhesive on the free ends of the attachment straps is preferably one that is high in shear strength but low in peel strength in reference to the thermoplastic moisture impervious backsheet of the diaper. This allows the straps to be easily removed and reattached if desired, but provides a firm grip while the garment is being worn.

12 Claims, 7 Drawing Figures

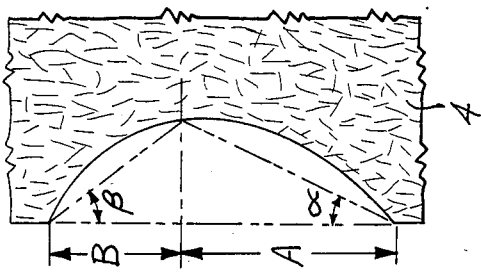
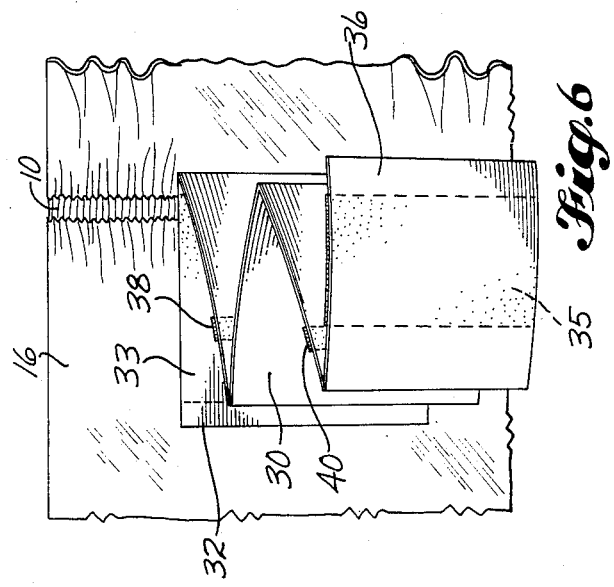
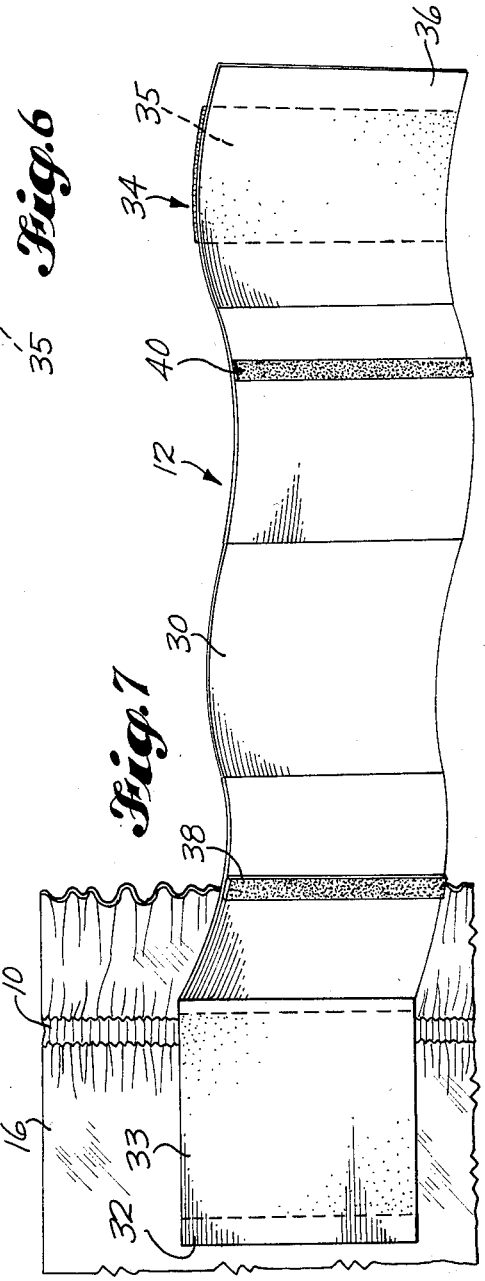
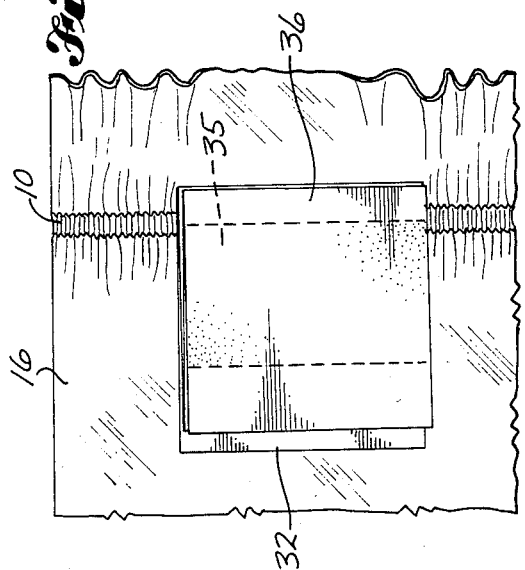

LEAK RESISTANT DIAPER OR INCONTINENT GARMENT

BACKGROUND OF THE INVENTION

The present invention is a diaper or incontinent brief which offers increased comfort for the wearer and which is highly resistant to leakage during use. One version of the pad has attachment straps which are releasable without tearing the moisture impervious backing film and which may later be reattached if desired.

Disposable diapers and similar products have gained wide acceptance in recent years. While these products are used mainly for infants prior to toilet training, they are also used for older children and adults with problems of bladder or bowel incontinence. Until very recently, most such adult products have completely encircled the hip region of the wearer so that they resemble a very bulky panty when in use. In the adult sizes in particular, this wrap-around construction results in large areas of skin being tightly covered in a moisture impervious garment. In hot weather, such a garment becomes very uncomfortable for the wearer. Recently, products have appeared on the market which are open at the sides and have somewhat the appearance of a loin cloth when worn. These products are finding excellent marketplace acceptance by the users since they are much cooler and generally more comfortable than the bulky products which have full hip enclosure. Additionally, these newer products are more economical to manufacture and more efficient in use because they do not place large volumes of the absorbent pad in areas so remote from the point of wetting that it is inefficiently utilized. One such product is disclosed in an earlier patent application of the present inventor, Ser. No. 06/476,675, filed Mar. 18, 1983. This attachment uses straps which are adhesively held in place but which may be later removed and then reapplied without damaging the thin plastic coversheet common to nearly all garments of this type. Another product of this type has recently appeared in the marketplace and is sold as Depend undergarments by the Kimberly-Clark Corporation, Neenah, Wis. Depend is a registered trademark of the manufacturer. This product uses button-on elastic straps to hold it in place on the wearer.

One problem which has received a great deal of attention is prevention of leakage in the thigh and waist areas of disposable diapers. Originally, this problem was attacked by the use of the so-called Z-fold configuration in which a folded portion near the edge of the diaper served somewhat as a seal to prevent leakage in the thigh area. However, the Z-fold configuration was only moderately successful in preventing leakage and had the additional disadvantage of placing a great deal of uncomfortable bulk in the crotch area of the wearer. Later inventors have tackled this problem with some success. U.S. Pat. No. 3,860,003 to Buell is one example. In this inventor's preferred construction, the pad and its enclosing envelope are trimmed in a generally hourglass-type configuration to reduce the bulk in the crotch area. Additionally, elastic strips are located along the margins in the crotch area so that in use these form seals against leakage as they are stretched around the thighs of the wearer. A modification of this construction is seen in U.S. Pat. No. 4,050,462 to Woon et al. In U.S. Pat. No. 4,253,461, Strickland et al. have also retained the narrowed crotch with elastic along the margins of the crotch area. In addition, they have provided an extra pair of attachment tapes to guarantee a tighter fit in the waist area.

The use of elastic margins on disposable diapers goes back well before the time of the above inventions. U.S. Pat. No. 2,273,542 to Tasker shows a rectangular diaper having full-length elastic inserts along each longitudinal margin. Tasker takes advantage of the additional bulk in the crotch area to form a pocket which is said to act as a waste receptacle.

In conventional diapers, an absorbent pad, usually of fluffed wood pulp enclosed within thin tissue layers, is retained within an envelope comprising a thin thermoplastic backsheet and a moisture impervious topsheet of non-woven material which is worn adjacent to the skin of the wearer. This envelope, as well as its included absorbent pad, has been assembled in many different configurations. The products currently finding considerable acceptance as infant diapers usually contain an hourglass-shaped pad within a similarly configured envelope of somewhat larger dimensions. Examples having this construction are seen in each of the aforementioned patents to Buell, Woon et al., and Strickland et al. However, it is known to put a generally hourglass configured pad within a rectangular envelope, as is seen in FIG. 6 of the Buell patent.

In pads having cutout portions to give them an hourglass-shaped configuration, it is normal for the longitudinal center of the cutout to be located on the transverse centerline of the diaper to create an essentially symmetrical configuration. The cutouts themselves do not necessarily show the front-to-back symmetry on either side of their centerline. Rather surprisingly, all of the asymmetrical cutout portions of which the present inventor is aware seem to widen out faster in the front portion of the diaper than they do in the back portion. A rather striking example of this is seen in U.S. Pat. No. 3,794,033 to Ryan.

Most of the significant design improvements to date in disposable diapers have been made in those intended for use on infants, since this represents the largest portion of the market for the product. When attention began to be directed toward disposable diapers or briefs for incontinent adults, the earlier products were simply scaled-up versions of those intended for infant use. These early products were not very satisfactory due to the obvious anatomical differences between infants and adults. They were hot, bulky, and uncomfortable for the wearer and leakage was an ever-present problem. Another problem was caused by the use of adhesive-coated attachment tapes. While these represent a distinct convenience in comparison to safety pins, in the past they could not be removed without tearing the thermoplastic backing sheet on the front of the diaper.

The present invention addresses all of the above problems and provides technically acceptable solutions which add little or nothing to the manufacturing cost of the articles.

SUMMARY OF THE INVENTION

The present invention comprises an improved disposable diaper or incontinent brief. This is of the general type which has a moisture absorbent pad contained within a coextensive envelope comprising a thin moisture impervious thermoplastic backsheet and a moisture pervious skin contacting nonwoven topsheet. The diaper is of generally rectangular configuration having longitudinal side portions which are longer than the transverse dimensions. The product is of a general configuration that does not enclose the sides of the wearer. Attachment straps are permanently bonded at their proximal ends near each back corner of the diaper. Each of these straps has an adhesive coated distal end for securing the diaper to a wearer. Elastic means are located adjacent to and parallel to each longitudinal edge of the diaper. Each elastic means runs essentially the full length of the garment. The moisture absorbent pad contained within the envelope has a cutout portion along each longitudinal side which gives it a generally hourglass-shaped configuration. This cutout portion is asymmetrically located front-to-back so that the longitudinal centers of the cutouts are located forward of the front-to-back transverse centerline of the pad. The pad is configured within the envelope so that when in use by a wearer the back edge of the diaper is located somewhat higher on the body than the front edge. In the most preferred version of the diaper, the backsheet and topsheet forming the envelope which contains the absorbent pad extend substantially beyond the ends of this pad to form flaps free of the absorbent filler material. These flaps preferably have a combined length from about 15–25% of the total length of the diaper. Most preferably, this combined length is about 20% of the total length of the diaper. The front flap will normally be from 20–120% longer than the rear flap.

The diaper configuration itself is relatively long and narrow. The overall width of the diaper will generally be within the range of 35–50% of the overall length.

The attachment straps will normally have their proximal ends permanently fixed to the upper corners of the rear flap and will have a length in the range of about 60–120% of the width of the diaper. These long straps can present a packaging problem. One satisfactory solution is to fold and retain them in accordion fashion until they are ready for use. The preferred versions of the straps will have an adhesive coating located near the distal ends that can be used to hold the straps firmly in place of the front portion of the diaper when it is in use. It is desirable that this adhesive coating have a relatively high shear strength but be low in peel strength against the backsheet so that the straps will hold firmly while in use, yet can be easily removed from the backsheet without damaging it. Then, if desired, they can be replaced in the same or a different location.

In the preferred construction of the diaper, the elastic means comprises narrow strips of an elastomeric material which are bonded to the backsheet in a position which either overlies or lies just outside the longitudinal line connecting the widest portions of the absorbent pad. Normally the backsheet and topsheet will be bonded together and extend laterally beyond the elastic means to form narrow longitudinal flanges which further help to seal the edges against the body of the wearer. Each flange will usually be from 5–10% of the total width of the diaper.

The cutout portions of the pad, in addition to having a center zone located forward of the transverse centerline of the pad, are also preferably asymmetric in their front-to-back configuration. A line or chord projected from the front end of the cutout portion to its deepest point will generally define a more acute angle with a longitudinal edge of the pad than will a similar set of lines or projections from the back end of the cutouts. Stated differently, the front end of the cutout portions will widen out less rapidly than will the back portions.

It is an object of the present invention to provide a disposable diaper or incontinent pad that is comfortable in use and which is highly resistant to leakage.

It is another object to provide a diaper or incontinent pad having attachment straps which may be released and later reapplied without damaging the garment.

It is a further object to provide a diaper or incontinent pad in which the sides of the wearer are not covered by the garment.

It is still another object to provide a diaper or incontinent pad which is simple to manufacture and which makes effective use of the contained absorbent material.

These and many other objects will become readily apparent upon reading the following detailed description taking in conjunction with the drawings.

BRIEF DESCRIPTION OF THE DRAWINGS

FIG. 4 is a detailed view of the cutout portion of the absorbent pad.

FIGS. 5 to 7 show details of one preferred form of attachment strap.

DESCRIPTION OF THE PREFERRED EMBODIMENTS

Figure 1:
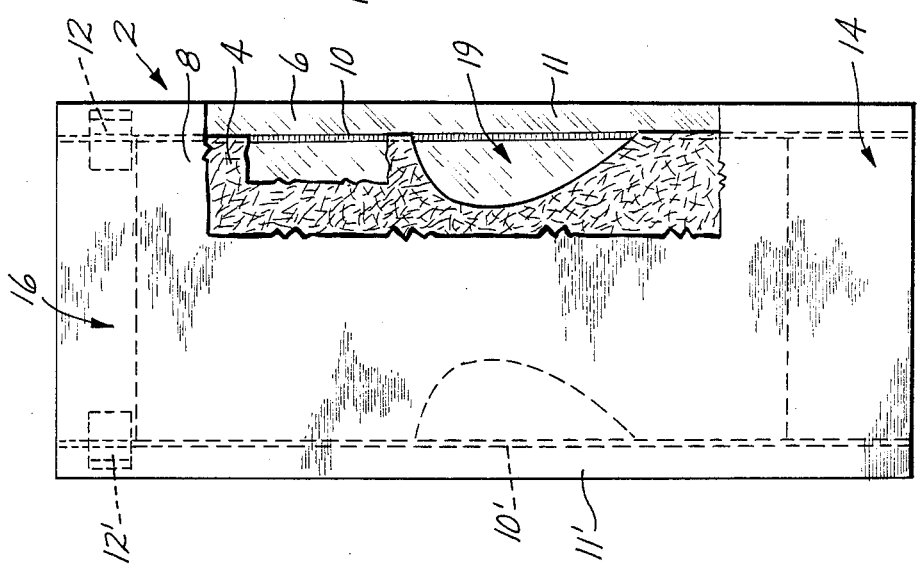
FIG. 1 is a plan view, partially cut away, of the present diaper or incontinent pad.

The present description contains the best mode known to the inventor of making the diaper or incontinent pad of the present invention. For the sake of simplicity, the following description will simply refer to the product as a diaper. Referring now to FIG. 1, the diaper, generally indicated at 2, comprises an absorbent cellulose pad 4 enclosed within an envelope formed from a moisture pervious backsheet 6 and a moisture pervious nonwoven topsheet 8. The backsheet and topsheet are adhesively bonded together along the margins to form an envelope for the pad. Preferably, they will be bonded in all areas where they are in contact by a series of narrow parallel adhesive lines 10–15 mm apart. In the normal method of manufacture, these narrow adhesive lines will be placed longitudinally for the full width of the backsheet so that they are effective to hold the moisture absorbent pad in position as well as bonding the topsheet in place. The pad will normally be made of air felted fluffed wood pulp but it could also be composed of multiple layers of an absorbent creped cellulose paper product. The backsheet 6 is normally a smooth or textured pigmented extruded polyethylene film about 0.025 mm (0.001 inch) in thickness. The topsheet 8 may be any compliant, soft nonwoven fabric web. These are normally formed of rayon or polyester fibers bonded with acrylic latices. Suitable products are available from several manufacturers well known within the industry.

Normally the first important manufacturing step is to place the lines of adhesive referred to earlier on the thermoplastic backsheet. This adhesive is normally a flexible hot melt product applied through an extruder. At about the same time the adhesive is applied, two bands of elastic, 10, 10′, are adhesively bonded to the backsheet. This elastic is normally a natural rubber product in the form of ribbons about 5 mm wide and about 0.2 mm in thickness. The elastic will typically be stretched to about 140–200% of its relaxed length before it is bonded to the backsheet. The backsheet is held under tension at this time so that the elastic remains in stretched condition. Following application of the elastic, the precut absorbent mats 4 are placed on the backsheet and immediately thereafter the topsheet is applied as a continuous strip. The assembly is then passed between light compression rolls to insure good bonding of the components. The next step in the process is the application of the attachment tape or strap units 12, 12' to what will become the back corners of the diaper. Finally, the individual diapers are severed from the continuous assembly and then folded and packaged for distribution and sale.

One of the novel features of the present invention is the provision of relatively wide flaps at each end of the product. These flaps represent extensions of the envelope beyond the portion which has the moisture absorbent pad. Relatively, narrow end flaps are common in diaper products and are necessary in order to seal the ends and better remain the absorbent material. However, in the present invention these flaps are considerably longer and have a combined length which should be from 15-25% of the total length of the diaper. In the preferred version of the diaper, the front flap 14 will be from 20-120% longer than the rear flap 16. The purpose of these flaps will be explained in more detail later. In general terms, thay are necessary to insure proper positioning and sealing of the garment on the wearer, yet they minimize the need for unnecessary and nonfunctional absorbent filler material.

Figure 3:
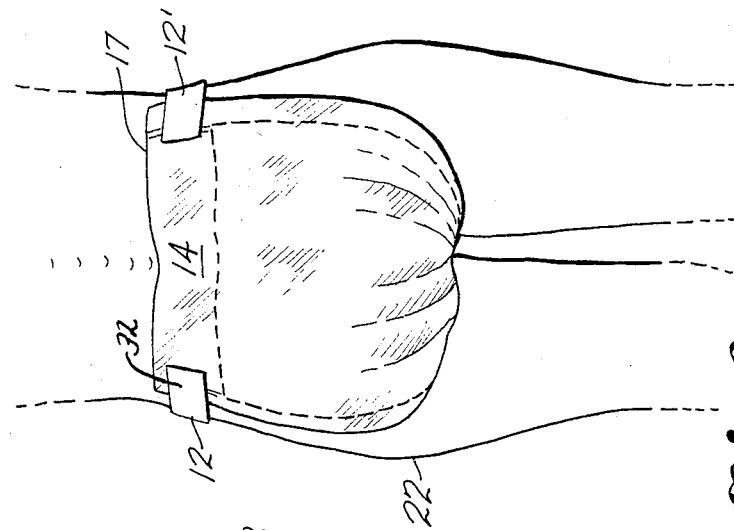
FIGS. 2 and 3 are front and back views, respectively, of the garment in place on a user.
Figure 2:
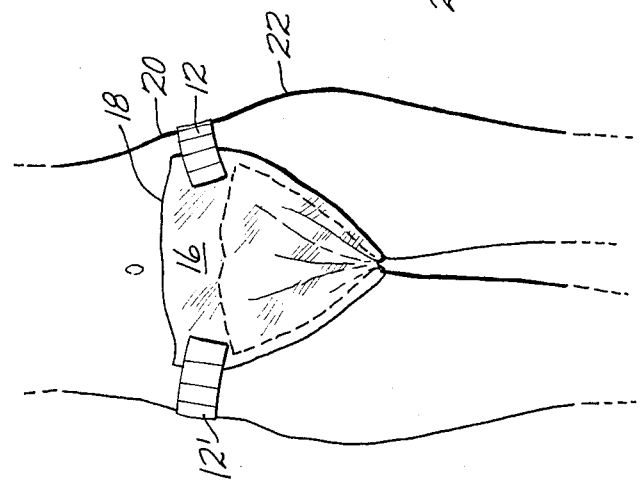

FIGS. 2 and 3 show front and back views of the garment on a wearer. The attachment straps 12 and 12' are permanently fixed to the back corners of the diaper and are located on rear flap 16. In FIG. 2, the distal ends are shown attached to the corresponding front flap 16. However, the attachment point on the front is not critical.

The diaper itself is a relatively long and narrow garment with a width in the range of 35-50% of the overall length. The attachment straps have a free length which is from 60-120% of the width of the diaper. The term "free length" excludes that portion of the attachment straps with is bonded to the back corners of the diaper.

As will be seen in FIGS. 2 and 3, the back edge 17 of the diaper is normally considerably higher on the body of the wearer than is the front edge 18. The exact positioning will depend somewhat on both the size of the diaper and the size of the individual wearing it. Back edge 17 should normally come almost to the natural waistline of the wearer, while the front edge 18 is somewhat below the waistline. This configuration allows the straps to hold the diaper firmly in place on the wearer without the need for excess materials. On a smaller individual, the straps 12, 12' will normally wrap around over the top of the wearer's hip bone 20. This point is defined by the iliac crest and the anterior superior iliac spine of the innominate bone. When worn on a somewhat larger individual, straps 12, 12' will wrap around below this point and lie in the slight hollow between the hip bone and the widest part of the hip 22, which is defined by the location of the greater trochanter of the femur. The attachment straps should thus angle somewhat downward from back-to-front when the garment is in use. With the particular length to width ratio heretofore defined for the diaper, it will not enclose the sides of the wearer. The elastic strips, 10, 10' are pretentioned so that when in use the diaper is held tightly against the buttocks in back and along the groin lines in front in a manner that practically eliminates any leakage.

One important feature of the present product that helps to position it properly on the wearer are the cutout areas 19 of the absorbent pad (FIG. 1). These cutout areas are placed with their front-to-back center points located forward of the front-to-back transverse centerline of the pad itself. The cutout areas are preferably asymmetrical in that the forward portion is longer and does not widen as rapidly as the rear portion of the cutout. FIG. 4 shows a typical cutout in which the length A, toward the front end, is approximately 50% longer than the length B. The angle $\alpha$ formed between a projection of the side of the diaper and a chord drawn from the end of the cutout to its deepest portion, will be smaller than the corresponding angle $\beta$ on the opposite side of the cutout. This configuration allows a better and more comfortable fit in the groin area.

The elastic ribbons 10, 10' are preferably located so that they are adjacent to or immediately outside of the absorbent pad 4. In the most preferred version of the product, they will lie somewhat inside the lateral edges of the envelope enclosing the pad so as to form flanges 11, 11'. Each of these flanges should normally be from 5-10% of the total width of the diaper. In conjunction with the elastic, they serve to further reduce leakage from the edges.

The attachment straps themselves form a unique and advantageous element of the product. Since these straps are much longer than the normal attachment tabs found in an infant diaper, they present a complex manufacturing and packaging product. This problem has been overcome by prefolding the straps in accordion-like fashion before they are applied to the diaper. As seen in FIGS. 5-7, the straps are formed from tape-like sections 30 made preferably from extruded thermoplastic sheet, although many other materials are suitable. The proximal end 32 of the straps is aggressively bonded by adhesive 33 to backsheet 6 on rear flap 16. The distal end 34 of the strap bears an adhesive area 35 and has an adhesive free terminal end 36. This adhesive is selected to have a low peel strength but a high shear strength against the backsheet so that it will hold the straps firmly in place when in use. However, the distal end of the straps can be readily peeled from their attachment point on the backsheet and then reattached if the diaper is not soiled and is suitable for reuse.

The straps may be folded by a number of different configurations. In a preferred one, adhesive area 35 is folded against the strap so that it is not exposed during shipping. The surface contacted by the adhesive area may be coated with a conventional release material so that it may be readily exposed for use by grasping tab end 36. The accordion pleats in the attachment strap can be easily held in place by narrow bands 38, 40 of a relatively weak adhesive. It will be evident to those skilled in the art that many other arrangements will be suitable. One product that has been found eminently satisfactory is available from 3-Sigma, Inc., Covington, Ohio. The strap itself is made of polypropylene film of about 0.10 mm (0.004 inches) in thickness with a width of about 400 mm and total length between about 350 and 460 mm. The free portion of the strap is approximately 30-40 mm shorter than the total length.

The peel strength between the backsheet and the distal end of the attachment straps should be in the range of 20-200N/m as measured by Pressure Sensitive Tape Counsel, Glenview, Ill., Test Method No. 1. This test method involves applying the surface being tested to a strip of adhesive approximately 13-25 mm wide and about 250 mm long. These are bonded together by the pressure of a rubber roller of predetermined characteristics which is passed over the adhesive area once in each direction. The material being tested is then pulled at an angle of 180° at a speed of 305 mm/minute with the required force being noted. The peel strength of the strap distal end adhesive from the backsheet is preferably in the range of about 50–150 N/m.

Bond strength between the adhesive at the distal end of the attachment straps and the backsheet should be sufficiently high in shear so that it will approach or exceed the failure point of the backsheet. No fully satisfactory test for measuring this property has been developed to data since the faces involved are complex. Tensile strength of the backsheet is probably the best measure of required bond strength. Thus, when loaded in shear, the bond strength between the distal ends of the attachment straps and the backsheet should approach or exceed the tensile strength of the backsheet. For the 0.025 mm polyethylene noted above the tensile strength is about 460 N/m (1200 g/in) across the machine direction and about 210 Nm (550 g/in) in the machine direction.

The adhesives used on the attachment straps and for assembly of the diaper itself are commercially available and are conventional within the art. The pressure sensitive adhesives used at the distal end of the attachment straps are usually based on modified natural rubbers or acrylic resins. This is normally formed or cast as a film directly on the surface of the attachment strap.

As one example of the present invention, adult incontinent pads were made in which the overall length of the envelope closing the absorbent pad was 760 mm and the width 330 mm. The overall dimensions of the absorbent cellulose pad were 610 mm long and 290 mm wide. The total weight of the completed diaper was 92 grams and the weight of the absorbent pad 68 grams. The absorbent pad was scalloped out along the sides to produce a crotch width of 152 mm, each side being cut into the pad a maximum depth of 69 mm. The narrowest part of the cutout portion was located 330 mm from the back edge and 280 mm from the front edge of the absorbent pad. The front portion of the cutout (dimension A of FIG. 4) was 152 mm long, and the rear portion (dimension B was approximately 102 mm in length. Angle $\alpha$ was $22\frac{1}{2}°$ and angle $\beta$ was 32°. The thermoplastic backsheet was micro-embossed polyethylene, 0.025 mm (0.001 inch) in thickness supplied by Visqueen Corp., Terre Haute, Ind. A nonwoven surface layer having a basis weight of 25 g/m² was supplied by Arkon Corp., Greenville, SC. The finished diaper could easily be applied to a wearer and removed several times without losing the integrity of the attachment tape bond and without damaging the backsheet.

Having now described the best known mode of practicing and carrying out the invention, it should be noted that there are many equivalent structures and materials which have not been described which will be considered by those skilled in the art to be within the scope of the invention. As one example, the cutout area of the absorbent pad need not be curvilinear in configuration but could be described by a pair of intersecting straight lines. As another example, many materials besides polypropylene film would be satisfactory for use as attachment straps. The invention should thus be considered as limited by only the following claims:

What is claimed is:

1. In a disposable diaper of incontinent brief having an essentially coextensive thin moisture impervious thermoplastic backsheet, a moisture absorbent cellulose pad, and a moisture previous skin contacting nonwoven topsheet, the diaper being of generally rectangular configuration having longitudinal side portions and transverse front and back end portions, the improvement which comprises:
   a. front and rear flap means formed by extensions of the backsheet and topsheet beyond the absorbent pad, the front flap being longer than the rear flap and the combined lengths of the flaps being from 15–25% of the total length of the diaper;
   b. two attachment straps means permanently bonded at their proximal ends to each rear flap means, each strap having an adhesive distal end for securing the diaper to a wearer and an adhesive free zone between the proximal and distal ends;
   c. elastic means located adjacent to and parallel to each longitudinal edge, each elastic means running essentially the full length of the diaper and serving to hold the edges of the brief in close leak-resisting contact with the body of the wearer;
   d. the moisture absorbent pad having a crotch area cutout portion along each longitudinal side to give it a generally hourglass-shaped configuration, the longitudinal centers of the cutout portions being located forward of the front-to-back transverse centerline of the pad so that when in use by a wearer the back edge of the diaper is located near the waistline and is higher on the body than the front edge, the crotch area cutout being formed so that the acute angle between a chord drawn from the front of the cutout to the deepest portion and a projection of the side of the diaper is smaller than the acute angle between the chord drawn from the rear of the cutout to the deepest portion and the side projection.

2. The diaper of claim 1 in which the front flap is from 20–120% longer than the rear flap.

3. The diaper of claim 1 in which the overall width of the diaper is from 35–50% of the overall length.

4. The diaper of claim 1 in which the free length of the attachment strap means if from 60–120% of the width of the diaper.

5. The diaper of claim 1 in which the attachment straps are folded in accordion fashion until ready for use.

6. The diaper of claim 1 in which the adhesive on the distal end of the attachment strap means is relatively high in shear strength and low in peel strength so that the straps will hold firmly in place when in use but can easily be removed from the backsheet without damage to the backsheet.

7. The diaper of claim 6 in which the peel strength between the adhesive at the distal end of the attachment strap means and the thermoplastic backsheet is in the range of 20–200 N/m.

8. The diaper of claim 6 in which the shear strength between the adhesive at the distal end of the attachment strap means and the thermoplastic backsheet is essentially equal to or greater than the tensile strength of the backsheet.

9. The diaper of claim 1 in which the elastic means is located at the edge of the absorbent fluff pad and the backsheet and topsheet extend beyond the elastic means to form narrow longitudinal flanges.

10. The diaper of claim 9 in which each flange is from 5–10% of the total width of the diaper.

11. The diaper of claim 1 in which the crotch area cutout is curvilinear in form.

12. The diaper of claim 1 in which the crotch area is formed from intersecting straight lines.

* * * * *

UNITED STATES PATENT AND TRADEMARK OFFICE
CERTIFICATE OF CORRECTION

PATENT NO. : 4,578,072

DATED : March 25, 1986

INVENTOR(S) : Eugene P. Lancaster

It is certified that error appears in the above—identified patent and that said Letters Patent is hereby corrected as shown below:

In column 5, line 18, "remain" should read --retain--;

In column 6, line 60, "400 mm" should read --40 mm--;

In column 7, line 14, "data" should read --date--;

In column 7, line 14, "faces" should read --forces--;

In column 7, line 21, "210 Nm" should read --210 N/m--;

In column 7, line 32, "envelope closing" should read --envelope enclosing--;

In column 7, line 68, "previous" should read --pervious--;

In column 8, line 39, "means if" should read --means is--;

Signed and Sealed this

Fifth Day of August 1986

[SEAL]

Attest:

DONALD J. QUIGG

Attesting Officer

Commissioner of Patents and Trademarks